United States Patent
Rivier et al.

(10) Patent No.: US 6,579,967 B1
(45) Date of Patent: Jun. 17, 2003

(54) RECEPTOR-SELECTIVE SOMATOSTATIN ANALOGS

(75) Inventors: Jean E. F. Rivier, La Jolla, CA (US); Jean Claude Reubi, Berne (CH)

(73) Assignee: The Salk Institute for Biological Studies, San Diego, CA (US)

( * ) Notice: Subject to any disclaimer, the term of this patent is extended or adjusted under 35 U.S.C. 154(b) by 0 days.

(21) Appl. No.: 09/607,546

(22) Filed: Jun. 29, 2000

Related U.S. Application Data

(63) Continuation-in-part of application No. 09/461,651, filed on Dec. 14, 1999, now abandoned.

(51) Int. Cl.$^7$ .................. A61K 38/31; C07K 16/00; C07K 17/00; C07K 2/00; C07K 4/00
(52) U.S. Cl. .................. 530/311; 530/300; 930/160
(58) Field of Search .................. 514/2, 9, 11; 530/300, 530/311; 930/160

(56) References Cited

U.S. PATENT DOCUMENTS

| | | | |
|---|---|---|---|
| 5,597,894 A | 1/1997 | Coy et al. | 530/311 |
| 5,750,499 A | 5/1998 | Hoeger et al. | 514/9 |
| 5,932,189 A | 8/1999 | Dean et al. | 424/1.69 |
| 5,955,426 A | 9/1999 | Dean et al. | 514/11 |
| 5,962,409 A | 10/1999 | Deghenghi | 514/11 |
| 5,972,308 A | 10/1999 | Dean | 424/1.69 |
| 5,976,496 A | 11/1999 | Dean et al. | 424/1.69 |
| 6,001,801 A | 12/1999 | Coy et al. | 514/9 |

FOREIGN PATENT DOCUMENTS

WO  WO 96/18642 A  6/1996

OTHER PUBLICATIONS

Hoeger, C.A. et al., "Betide Based Strategy for the Design of GnRH and Receptor Selective Somatostatin Analogs", Peptides: Chemistry, Structure and Biology, Proceedings of the American Peptide Symposium, 14$^{th}$, Columbus, Ohio (1996).
Reubi, J.C. et al., "SST3–Selective Potent Peptidic Somatostatin Receptor Antagonists", P.N.A.S., vol. 97, No. 25, Dec. 5, 2000, pp. 13973–13978.
Hocart, S.J. et al., Highly Potent Disulfide Antagonists of Somatostatin, J. Med. Chem., vol. 42, No. 11, Jun. 3, 1999, pp. 1863–1871.
Rohrer, S.P. et al., "Rapid Identification of Subtype–Selective Agonists of the Somatostatin Receptor Through Combinatorial Chemistry", Science, vol. 282 (5389), (Oct. 23, 1998), pp. 737–740.
Rossowski, W. J. et al., "Specific Inhibition of Rat Pancreatic Insulin or Glucagon Release by Receptor–Selective Somatostatin Analogs", B.B.R.C., vol. 205, No. 1, 1994, pp. 341–346.
Virgolini et al., "In Vitro and In Vivo Studies of Three Radiolabelled Somatostatin Analogues: $^{123}$I–Octreotide (OCT), $^{123}$I–Tyr–3–OCT and $^{111}$In–DTPA–D–Phe–1–OCT", European Journal of Nuclear Medicine, vol. 23, No. 10, pp. 1388–1399, Oct. 1996.
De Jong et al., "Pre–Clinical Comparison of [DTPA$^0$] Octreotide, [DTPA$^0$, Tyr$^3$] Octreotide and [DOTA$^0$, Tyr$^3$] Octreotide as Carriers for Somatostatin Receptor–Targeted Scintigraphy and Radionuclide Therapy", Int. J. Cancer, vol. 75, 406–411 (1998).
Jiang, et al., "Orthogonally Protected N–Methyl–Substituted α–Aminoglycines", Protein and Peptide Letters, vol. 3, No. 4, pp. 219–224 (1996).

Primary Examiner—Gary Kunz
Assistant Examiner—Robert S. Landsman
(74) Attorney, Agent, or Firm—Fitch, Even, Tabin & Flannery

(57) ABSTRACT

Analogs of SRIF which are selective for SSTR3 in contrast to the other cloned SRIF receptors. These analogs are useful in determining the tissue and cellular expression of the receptor SSTR3 and its biological role in the endocrine, exocrine and nervous system, as well as in regulating tumor growth. SRIF analog peptides, such as des-AA$^{1,2,4,5,12,13}$ [N$^\beta$MeD-Agl$^8$(2-naphthoyl) ]-SRIF and counterparts incorporating D-Cys$^3$ and/or Tyr$^7$, inhibit the binding of a universal SRIF radioligand to the cloned human receptor SSTR3, but they do not bind with significant affinity to human SSTR1, SSTR2, SSTR4 or SSTR5. By incorporating an iodinated tyrosine in position-2 or in position-11 in these SSTR3-selective SRIF analogs, a labeled compound useful in drug-screening methods is provided. Because the N-terminus accommodates bulky moieties without loss of selectivity, a cytotoxin or a complexing agent to accept a radioactive nuclide may be present at the N-terminus. Alternatively, the binding affinity may be improved without detriment to the selectivity by adding a carbamoyl moiety at the N-terminus and/or replacing Phe$^{11}$ with Aph or substituted Aph.

14 Claims, No Drawings

RECEPTOR-SELECTIVE SOMATOSTATIN ANALOGS

This application is a continuation-in-part of our earlier application Ser. No. 09/461,651, filed Dec. 14, 1999, now abandoned, the disclosure of which is expressly incorporated herein by reference.

This invention was made with Government support under Grant No. 5R01 DK50124 awarded by the National Institutes of Health. The Government has certain rights in this invention.

This invention is directed to peptides related to somatostatin and to methods for pharmaceutical treatment of mammals using such peptides. More specifically, the invention relates to shortened receptor-selective somatostatin analogs and the inclusion of an amino acid substitution in such analogs that confers receptor-selectivity thereto, to pharmaceutical compositions containing such peptides, to such peptides complexed with radioactive nuclides or conjugated to cytotoxins, to methods of diagnostic and therapeutic treatment of mammals using such peptides, particularly peptides that are chelated or otherwise labelled, and to methods for screening for more effective drugs using such peptides.

BACKGROUND OF THE INVENTION

The cyclic tetradecapeptide somatostatin-14 (SRIF) was originally isolated from the hypothalamus and characterized as a physiological inhibitor of growth hormone release from the anterior pituitary. It was characterized by Guillemin et al. and is described in U.S. Pat. No. 3,904,594 (Sep. 9, 1975). This tetradecapeptide has a bridging or cyclizing bond between the sulfhydryl groups of the two cysteinyl amino acid residues in the 3- and 14-positions. SRIF was found to also regulate insulin, glucagon and amylase secretion from the pancreas, and gastric acid release in the stomach, e.g. it inhibits the effects of pentagastrin and histamine on the gastric mucosa. SRIF is also expressed in intrahypothalamic regions of the brain and has a role in the regulation of locomotor activity and cognitive functions. SRIF is localized throughout the central nervous system, where it acts as a neurotransmitter. In the central nervous system, SRIF has been shown to both positively and negatively regulate neuronal firing, to affect the release of other neurotransmitters, and to modulate motor activity and cognitive processes.

Somatostatin and many analogs of somatostatin exhibit activity in respect to the inhibition of growth hormone (GH) secretion from cultured, dispersed rat anterior pituitary cells in vitro; they also inhibit GH, insulin and glucagon secretion in vivo in the rat and in other mammals. One such analog is [D-Trp$^8$]-SRIF which has the amino acid sequence: (cyclo 3-14)H-Ala-Gly-Cys-Lys-Asn-Phe-Phe-D-Trp-Lys-Thr-Phe-Thr-Ser-Cys-OH, which is disclosed in U.S. Pat. No. 4,372,884 (Feb. 8, 1983). Somatostatin has also been found to inhibit the secretion of gastrin and secretin by acting directly upon the secretory elements of the stomach and pancreas, respectively, and somatostatin is being sold commercially in Europe for the treatment of ulcer patients. The powerful inhibitory effects of somatostatin on the secretion not only of GH but also of insulin and glucagon have led to studies of a possible role of somatostatin in the management or treatment of juvenile diabetes and have proved useful in studying the physiological and pathological effects of these hormones on human metabolism. SRIF is also known to inhibit the growth of certain tumors.

L. Pradayrol, et al. in *FEBS Letters* 109, January 1980, pages 55–58, reported the isolation and characterization of somatostatin-28 (SRIF-28) from porcine upper small intestine. SRIF-28 is an N-terminally extended version of SRIF which has an additional 14 amino acid residues and which shows some increased potency when administered in vivo.

SRIF affects multiple cellular processes. Studies have shown that SRIF is an inhibitory regulator of adenylyl cyclase in different tissues. SRIF also regulates the conductance of ionic channels, including both $K^+$ and $Ca^{2+}$ channels. These actions of SRIF are mediated via pertussis toxin-sensitive guanine nucleotide-binding proteins. SRIF also regulates the activity of tyrosine phosphatases, the $Na^+/H^+$ antiport, and cellular proliferation through pertussis toxin-insensitive mechanisms.

SRIF induces its biological effects by interacting with a family of membrane-bound structurally similar receptors. Five SRIF receptors have been cloned and are referred to as SSTR1–5. Human SSTR1, mouse SSTR2 and mouse SSTR3 are described in Raynor et al., *Molecular Pharmacology*, 43, 838–844 (1993), and all five human SRIF receptors are now available for research purposes. Human SSTR1, 2 and 3 are also disclosed in U.S. Pat. No. 5,436,155 (Jul. 25, 1995). Additional SRIF receptors are disclosed in U.S. Pat. No. 5,668,006 (Sep. 16, 1997) and 5,929,209 (Jul. 27, 1999). All five receptors bind SRIF and SRIF-28 with high affinity. Selective agonists at SSTR2 and SSTR5 have been identified and used to reveal distinct functions of these receptors. These two receptors are believed to be the predominant subtypes in peripheral tissues. SSTR2 is believed to mediate the inhibition of growth hormone, glucagon and gastric acid secretion. In contrast, SSTR5 appears to be primarily involved in the control of insulin and amylase release. SSTR3 is found in cortex tissue, in the pituitary and in ademoma tumor tissue; it is believed to mediate inhibition of gastric smooth muscle contraction upon binding by SRIF. These findings indicate that different receptor subtypes mediate distinct functions of SRIF in the body.

There are different types of tissues in the human body that express somatostatin receptors including: (1) the gastrointestinal tract, likely including the mucosa and smooth muscle, (2) the peripheral nervous system, (3) the endocrine system, (4) the vascular system and (5) lymphoid tissue, where the receptors are preferentially located in germinal centers. In all these cases, somatostatin binding is of high affinity and specific for bioactive somatostatin analogs.

Somatostatin receptors are also expressed in pathological states, particularly in neuroendocrine tumors of the gastrointestinal tract. Most human tumors originating from the somatostatin target tissue have conserved their somatostatin receptors. It was first observed in growth hormone producing adenomas and TSH-producing adenomas; about one-half of endocrine inactive adenomas display somatostatin receptors. Ninety percent of the cardinoids and a majority of islet-cell carcinomas, including their metastasis, usually have a high density of somatostatin receptors. However, only 10 percent of colorectal carcinomas and none of the exocrine pancreatic carcinomas contain somatostatin receptors. The somatostatin receptors in tumors can be identified using in vitro binding methods or using in vivo imaging techniques; the latter allow the precise localization of the tumors and their metastasis in the patients. Because somatostatin receptors in gastroenteropancreatic tumors are functional, their identification can be used to assess the therapeutic efficacy of an analog to inhibit excessive hormone release in the patients.

A cyclic SRIF analog, variously termed SMS-201-995 and Octreotide, i.e. D-Phe-c[Cys-Phe-D-Trp-Lys-Thr-Cys]-

Thr-ol is being used clinically to inhibit certain tumor growth; analogs complexed with $^{111}$In or the like are also used as diagnostic agents to detect SRIF receptors expressed in cancers. Two similar octapeptide analogs having 6-membered rings, i.e. Lanreotide and Vapreotide, have also been developed, see Smith-Jones et al., *Endocrinology*, 140, 5136–5148 (1999). A number of versions of these somatostatin analogs have been developed for use in radioimaging or as radiopharmaceuticals in radionuclide therapy. For radioimaging, for example, labeling with $^{123}$I can be used as disclosed in U.K. Patent Application 8927255.3 and as described in Bakker et al., 1991, *J. Nucl. Med.*, 32:1184–1189. Proteins have been previously radiolabeled through the use of chelating agents, and there are various examples of complexing somatostatin analogs with $^{99}$Tc, $^{90}$Y or $^{111}$In, see U.S. Pat. Nos. 5,620,675 and 5,716,596. A variety of complexing agents have been used including DTPA (Dirgolini, et al., *European Journal of Nuclear Medicine*, 23:1388–1399, October 1996); (Stabin, et al., *J. Nuc. Med.*, 38:1919–1922, December 1997); (Vallabhajosula, et al., *J. Nuc. Med.*, 37:1016–1022, June 1996); DOTA (De Jong, et al., *Int. J. Cancer*, 75:406–411, 1998); (Froidevaux, et al., *Peptide Science-Present and Future*, 670–673, 1999); HYNIC (Decristoforo, et al. Eur. J. Nuc. Med., 26:869–876); (Krois, et al., *Liebigs Ann.*, 1463–1469, 1996); and $P_2S_2$-COOH (Karra, et al., *Bioconjugate Chem.*, 10:254–260, 1999. U.S. Pat. No. 5,597,894 discloses analogs of Octreotide modified to facilitate radiolabeling.

Octreotide and other clinically used SRIF analogs interact significantly with three of the receptor subtypes, i.e. SSTR2, SSTR3 and SSTR5. SSTR2 and SSTR5 have recently been reported to mediate antiproliferative effects of SRIF on tumor cell growth; therefore, they may mediate the clinical effects of Octreotide in humans. U.S. Pat. No. 5,750,499 (May 12, 1998) discloses SRIF analogs which are selective for SSTR1. A recent comprehensive review of SRIF and its receptors is found in Patel, Y. C. "Somatostatin and its receptor family", *Front. Neuroendocrinol*, 1999, 20, 157–198.

SSTR3 was one of the first SRIF receptors cloned. It has high affinity for SRIF and SRIF-28 but low affinity for most synthetic analogs of SRIF. In a variety of human tumors, SSTR3 mRNA is the most frequently and most strongly expressed subtype receptor among the SST receptors. Virgolini et al, *Eur. J. Clin. Invest.*, 27:645–647 (1997) reports such receptors on intestinal adenocarcinomas, and neuroendocrine tumors. As a result, the peptide radiopharmaceuticals that have been developed have been found to be useful for detection and visualization of tumors bearing somatostatin receptors, and those compounds that contain a complex with $^{111}$In or $^{90}$Y are very promising radioligands for receptor-mediated radiotherapy. SSTR3 is therefore considered to be an important target both for the physiological actions of SRIF and for certain therapeutic actions of SRIF analogs.

Because of the presence of SSTR3 on tumors, and because of the otherwise ubiquitous nature of the somatostatin receptors, it would be valuable to have somatostatin analogs that would bind strongly to SSTR3 while at the same time showing only minimal propensity for binding to SSTR1-2 and SSTR4-5. The search has continued for somatostatin analogs which are more potent than somatostatin and/or exhibit dissociated inhibitory functions, and particularly for analogs which are selective for SSTR3. Nonpeptide SRIF agonists have been identified using combinatorial chemistry which exhibit selectivity for each of SSTR1 to SSTR5, Rohrer, S. P. et al., *Science*, 282, 737–740, Oct. 23, 1998. However, no peptide ligand has thus far been available that selectively binds to SSTR3 and exhibits fairly high affinity, as a result of which efforts to determine the precise localization of SSTR3 in the body and to identify its biological actions have been hindered; moreover, this lack of selective SSTR3 peptide ligands having relatively high affinity has hampered efforts to design more selective tumor treatment and radionuclide therapy, because only peptide ligands can be satisfactorily derivatized to incorporate complexing agents for radionuclides.

SUMMARY OF THE INVENTION

Certain modifications have now been discovered which are effective to create peptide analogs of SRIF that are selective for SSTR3 in contrast to the other cloned SRIF receptors. The preferred modification substitutes $N^\beta$MeAgl (Np) into the 8-position of a SRIF analog that otherwise binds to SSTR3, and the binding strength of such analog can be enhanced by an optional modification at the N-terminus and/or in the 11-position. As a result, peptides have now been created that bind selectively to cloned SSTR3, and analogs of these peptides can be iodinated or otherwise radiolabeled while retaining their desirable biological properties. These novel peptides are useful in determining the tissue and cellular expression of the receptor SSTR3 and its biological role in the endocrine, exocrine and nervous system, as well as in regulating certain pharmacological functions without the accompanying side effects heretofore characteristic of administering SRIF. These long-acting SRIF analog peptides, when radiolabeled, can be used in scintigraphy in order to locate, i.e. localize, tumors expressing these receptors, either in vitro or in vivo; other labeling as well known in this art, e.g. fluorescent, can alternatively be used. With an appropriate chelated radioligand, these analogs can be turned into radiopharmaceuticals which are suitable for radionuclide therapy in treatment of such tumors; alternatively, they can be covalently joined to a cytotoxic moiety using an appropriate covalent conjugating agent, e.g. glutaraldehyde or one which binds via a disulfide linkage.

The SRIF analog peptides of the invention inhibit the binding of $^{125}$I-[Tyr$^{11}$]SRIF and $^{125}$I-[Leu$^{8}$,D-Trp$^{22}$,Tyr$^{25}$] SRIF-28 to the cloned human receptor SSTR3, but they do not strongly bind to SSTR1, SSTR2, SSTR4 or SSTR5. Additional of these SRIF analogs which incorporate an iodinated tyrosine in position-2 of the native molecule also do not bind to SSTR1, 2, 4 or 5 but still bind potently and saturably to SSTR3. This is also true for analogs to which $^{99}$Tc, $^{111}$In or $^{90}$Y, for example, has been chelated by linkers, such as DOTA or DTPA, or to which other complexing or conjugating agents are linked to the N-terminus for the purpose of attaching moieties useful for diagnostic or therapeutic purposes.

Many of these SRIF analogs not only selectively bind to SSTR3, but they bind thereto with high affinity. By selectively binding is meant that they exhibit a $K_D$ or an $IC_{50}$ with SSTR3 which is about one-tenth or less of that with respect to at least 3 of the other five SRIF receptors. It is believed the four residues located centrally within the ring structure, i.e. at positions 7–10 of the native molecule, are primarily responsible for receptor binding and biological activity. These SRIF analogs can also be readily labeled and effectively used in drug screening methods and in radionuclide and cytotoxic therapy. For example, these analogs are useful in localizing such receptor in the body and in diagnosing the locations of tumors, particularly neuroendocrine tumors. As radionuclide therapeutic agents, they are considered to be particularly useful in combating tumors mediated by the SSTR3 receptors, as demonstrated by [$^{90}$Y-DOTA-Tyr$^3$]-Octreotide; however, they are able to accomplish this without the side effects that would otherwise accompany administration of currently available Octreotide analogs which have a propensity to interact with a plurality of SRIF receptors, i.e. SSTR2, SSTR3 and SSTR5.

DETAILED DESCRIPTION OF THE PREFERRED EMBODIMENTS

Unless defined otherwise, all technical and scientific terms used herein have the same meaning as is commonly understood by one of skill in the art to which this invention belongs. The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine. By D,L is meant a mixture of the D- and L-isomers of a particular α-amino acid.

SRIF analog peptides are provided having a selective affinity for the SRIF receptor SSTR3; the preferred analogs also have a high affinity for SSTR3, i.e. equal to a $K_D$ of about 10 nanomolar or less. These peptides broadly encompass known analogs of SRIF, or obvious variations thereof, which either have a D-isomer amino acid having a particular aromatic side chain in the position corresponding to the 8-position of the native peptide or have an L-isomer amino acid of this same general character in the position that corresponds to the 7-position of the native peptide. To create this particular specificity, preferably the 8-position residue should be N$^\beta$MeD-Agl(Np); alternatively, the 7-position residue may be N$^\beta$MeAgl(Bz). So long as the basic analog being modified exhibits SRIF properties by binding generally to SRIF receptors, insertion of such a residue in the corresponding 7- or 8-position will create a molecule which is highly selective for the SSTR3 receptor. Preferably the 1-, 2-, 4-, 5-, 12- and 13-position residues are deleted to increase binding affinity to SSTR3.

Since the characterization of SRIF, a large number of SRIF analogs have been synthesized having increased potency in some respect. The following U.S. patents are illustrative of such SRIF analogs, which analogs can be rendered selective for the SSTR3 receptor by the incorporation of the modification of the present invention: U.S. Pat. Nos. Re. 30,548; 4,133,782; 4,211,693; 4,316,891; 4,372,884; 4,393,050; 4,061,608; 4,081,433; 4,182,707; 4,190,575; 5,185,010; 4,215,039; 4,230,617; 4,238,481; 4,253,998; 4,282,143; 4,328,214; 4,358,439; 4,209,441; 4,210,636; 4,316,890; and 5,073,541.

Examples of representative peptides exhibiting the desired specificity for SSTR3 are provided by the following amino acid sequence, which is based upon a numbering system consistent with the 14-residue sequence of native mammalian SRIF, but in which the residues at positions 4–5 and 12–13 have been eliminated: (cyclo 3-14)Xaa$_1$-Xaa$_2$-Xaa$_3$-Phe-Xaa$_7$-D-Xaa$_8$-Lys-Thr-Xaa$_{11}$-Cys wherein Xaa$_1$ is des-Xaa, Ala, D-Ala, Cbm, L-Hor, an acyl group having up to 7 carbon atoms, e.g. 4-hydroxybenzoyl, or alkyl (C$_1$ to C$_6$); Xaa$_2$ is Tyr, D-Tyr, Gly or des-Xaa; -Xaa3 is Cys or D-Cys; Xaa$_7$ is an amino acid selected from the group consisting of (A)Phe, Tyr, or N$^\beta$MeAgl(Bz) wherein A is H, Cl, F, Br, NO$_3$, Me OMe or NH(Q) where Q is H, Cbm or L-Hor; D-Xaa$_8$ is an amino acid selected from the group consisting of D-Nal and N$^\beta$MeD-Agl(Np), provided that either Xaa$_7$ is N$^\beta$MeAgl(Bz) or D-Xaa$_8$ is N$^\beta$MeD-Agl(B); and Xaa$_{11}$ is Phe, Aph(X) or Tyr, with X being H, Ac or Cbm. A tyrosine residue at position 2, 7 or 11 may be radioiodinated without adversely affecting binding affinity; however, when such a radiolabelled analog is created, radio-iodination of Tyr$^2$ or Tyr$^{11}$ is preferred. As previously indicated, a complexing agent can be linked to the α-amino group at the N-terminal of any of these peptide analogs which is capable of joining thereto a radioactive nuclide or a cytotoxin.

One preferred subgenus of SRIF analogs has the amino acid sequence:

(cyclo 3-14)Xaa$_1$-Xaa$_2$-Xaa$_3$-Phe-Xaa$_7$-D-Xaa$_8$-Lys-Thr-Xaa$_{11}$-Cys wherein Xaa$_1$ is Cbm; Xaa$_2$ is Tyr, D-Tyr or des-Xaa; Xaa$_3$ is Cys or D-Cys; Xaa$_7$ is (A)Phe or Tyr; and D-Xaa$_8$ is N$^\beta$MeD-Agl(Np). The remaining variables are as defined hereinbefore whenever they are not specified.

Another preferred subgenus of SRIF analogs has the amino acid sequence:

(cyclo 3-14)Xaa$_1$-Xaa$_2$-Xaa$_3$-Phe-Xaa$_7$-D-Xaa$_8$-Lys-Thr-Xaa$_{11}$-Cys wherein Xaa$_1$ is Cbm or des-Xaa; Xaa$_2$ is Tyr, D-Tyr or des-Xaa; Xaa$_3$ is Cys or D-Cys; Xaa$_7$ is N$^{62}$ MeAgl(Bz); and D-Xaa$_8$ is D-Nal.

An additional preferred subgenus of SRIF analogs has the amino acid sequence:

(cyclo 3-14) Xaa$_2$-D-Cys-Phe-Xaa$_7$-D-Xaa$_8$-Lys-Thr-Xaa$_{11}$-Cys wherein Xaa$_2$ is Tyr, D-Tyr or des-Xaa; Xaa$_7$ is Phe or Tyr; D-Xaa$_8$ is N$^\beta$MeD-Agl(Np); and Xaa$_{11}$ is Phe or Aph(X).

Still another preferred subgenus of SRIF analogs has the amino acid sequence:

(cyclo 3-14) Xaa$_1$-Xaa$_2$-D-Cys-Phe-Xaa$_7$-D-Xaa$_8$-Lys-Thr-Xaa$_{11}$-Cys wherein Xaa$_1$ is Cbm or des-Xaa$_1$; Xaa$_2$ is Tyr, D-Tyr or des-Xaa; Xaa$_7$ is N$^\beta$MeAgl (benzoyl); D-Xaa$_8$ is D-2Nal; and Xaa$_{11}$ is Phe or Aph(X).

By D-Nal is meant the D-isomer of alanine which is substituted by naphthyl on the β-carbon atom. D-2Nal, wherein the attachment to naphthalene is at the 2-position on the ring structure, is preferable; however, D-1Nal is generally equivalent. Cbm stands for carbamoyl and is preferred; however, lower alkyl carbamoyl, e.g. methyl isopropyl, butyl, etc., are considered to be equivalents. By Me is meant methyl. By Bzl is meant benzyl, and by Bz is meant benzoyl. By Aph is meant aminophenylalanine, preferably 4Aph. By Ac is meant acetyl, and by Np is meant naphthoyl. By Agl is meant aminoglycine; it is always present in a form wherein the beta-amino group is alkylated with a methyl group and also acylated. It is present as the L-isomer when used in the 7-position and as the D-isomer when used in the 8-position. By Hor is meant the L-isomer of hydroorotic acid. As used herein, naphthoyl is inclusive of 1- and 2-naphthoyl, with 2-naphthoyl being preferred. By SRIF is meant the 14-residue cyclic peptide, somatostatin.

The C-terminus is usually free acid, although an equivalent, e.g. OMe or NH$_2$, might be used. The N-terminus may be modified in various ways without significantly adversely effecting the binding affinity, all of which modifications in these cyclic peptides are considered to be included as a part of the peptides of the overall invention. For example, a variety of additions may be made to the N-terminal amino acid in the form of complexing or conjugating agents which can be then used to join a desired moiety to the peptide. For example, chelating agents, such as DTPA, DOTA, HYNIC and $P_2S_2$-COOH may be attached; alternatively, a cytotoxin may be covalently linked thereto via a conjugating agent if desired. When either Tyr or D-Tyr appears at the N-terminus, it may be in the "desamino" form and/or may be radioiodinated or otherwise labeled. Acyl groups having not more than about 20 carbon atoms, e.g. 4-hydroxybenzyl, may also be present at the N-terminus, as bulky moieties appear to be accommodated without loss of selectivity.

Although SSTR3 was one of the first somatostatin receptors cloned, identification of its biological and pharmacological properties has lagged somewhat behind the other SRIF receptors because of the lack of ligands which are significantly selective for SSTR3. The peptides of the invention are believed to be the first truly SSTR3-selective peptides, and for a number of reasons it is considered advantageous to have peptide, rather than nonpeptide, ligands of this character. They will be very helpful in determining the many functional roles of this receptor and in selectively binding only this SRIF receptor and not the others, and they will be particularly valuable in SRIF receptor-targeted scintigraphy and radionuclide therapy.

Selectivity for binding of the analog peptides of the invention to SSTR3 was demonstrated by testing their interaction with the five different cloned human SRIF receptors as described in great detail hereinafter. Generally, recombinant cells expressing the receptor are washed and homogenized to prepare a crude protein homogenate in a suitable buffer, as known in the art. In a typical assay, an amount of protein from the cell homogenate is placed into a small volume of an appropriate assay buffer at an appropriate pH. Candidate substances, such as potential SRIF agonists and antagonists, are added to the admixture in convenient concentrations, and the interaction between the candidate substance and the receptor polypeptide is monitored. The peptides of the invention bind substantially only to SSTR3, and their binding exhibits high affinity.

Receptor binding assays are performed on cloned SRIF receptors as generally set forth in Raynor et al. supra. Using such assays, one can generate $K_D$ values which are indicative of the concentration of a ligand necessary to occupy one-half (50%) of the binding sites on a selected amount of a receptor or the like, or alternatively, competitive assays can generate $IC_{50}$ values which are indicative of the concentration of a competitive ligand necessary to displace a saturation concentration of a target ligand being measured from 50% of binding sites. The peptide des-AA$^{1,2,4,5,12,13}$-[D-Agl$^8$(Me,2-naphthoyl)]SRIF inhibits the binding to SSTR3 of an iodinated SRIF-28 ligand that has strong affinity for all five receptors. Testing shows that it binds to the cloned human SSTR3 with an $IC_{50}$ of about 70 nM, while this SRIF analog peptide does not bind to human SSTR1, SSTR2, or SSTR5 at concentrations below 10,000 nM nor to SSTR4 at a concentration below 1,000 nM.

When this SRIF analog is modified to have a tyrosine residue in position-2 which is then radioiodinated, testing for binding to the cloned human SRIF receptors shows the $^{125}$I-Tyr$^2$ analog likewise did not bind to SSTR1, 2, 4 or 5, but continues to bind saturably to SSTR3. Another exemplary analog, des-AA$^{1,2,4,5,12,13}$-[Agl$^7$(Me,Bz), D-2Nal$^8$]-SRIF inhibits binding of the same iodinated SRIF-28 ligand to SSTR3 and binds itself with an $IC_{50}$ of about 80 nM, while not binding to any of the other 4 receptors at concentrations below 1000 nM. These SRIF analogs that selectively show high affinity to SSTR3 are considered to be particularly useful in combating tumors by carrying radionuclides or cytotoxins to the sites of these receptors but not to other SRIF receptors.

As hereinbefore indicated, SSTR3 mRNA has been detected in a variety of tumors. However, it is presently not known whether SSTR3 plays a major role in tumor growth regulation and, if it does, whether it mediates simulation or inhibition. Therefore, it is difficult to foretell whether a selective SSTR3 antagonist would have a beneficial role for long-term treatment of tumors. However, the use of SRIF analogs selective for SSTR3 that bind strongly thereto, and that are long-acting can be effectively used to kill such tumors via radionuclide or cytotoxic therapy. To date the use of Octreotide in the treatment of such tumors has not been considered to be satisfactorily effective.

Although an analog of Octreotide has been employed to detect human tumors having high expression of SRIF receptors through the use of positron-emission tomography, this SRIF analog does not distinguish among SSTR2, SSTR3 and SSTR5. In comparison, radiolabeled SRIF analogs of the present invention can be employed for similar purposes, and they are considered to be specifically useful in identifying tumors expressing SSTR3, which tumors are then therapeutic targets for treatment with SSTR3-selective ligands as mentioned hereinbefore.

The SRIF analogs of the present invention are the first peptide analogs truly selective for SSTR3 and are considered to be useful in combating cancers which express SSTR3. They are also considered to be most useful in scintigraphy to determine the distribution of cells and tissues expressing this receptor in the brain and in the endocrine and exocrine systems, and also in identifying selective functions of this receptor in the body. They are further useful for treating non-neoplastic disorders linked to SSTR3-expressing tissues, such as have been found in the GI track smooth muscles. In other words, SSTR3 antagonists may be useful to treat gastrointestinal motility disorders.

Labeled SRIF analogs of the invention are also considered to be useful in drug-screening assays to screen for new effective peptide and nonpeptide agents which will bind with high affinity to SSTR3 and which may be either highly effective agonists or antagonists for treating GI track motility. Once a known ligand for the receptor SSTR3 is in hand, one can obtain a baseline activity for the recombinantly produced receptor. Then, to test for inhibitors or modifiers, i.e. antagonists of the receptor function, one can incorporate into a test mixture a candidate substance to test its effect on the receptor. By comparing reactions which are carried out in the presence or absence of the candidate substance, one can then obtain information regarding the effect of the candidate substance on the normal function of the receptor. The cyclic SRIF analogs described in Examples 2–2E hereinafter are antagonists and can be employed to selectively inhibit the normal function of SSTR3.

The peptides of the present invention can be synthesized by classical solution synthesis, but they are preferably synthesized by solid-phase technique. A chloromethylated resin or a hydroxymethylated resin is preferably used. For example, these peptides having a free carboxyl C-terminus are preferably synthesized as taught in U.S. Pat. No. 4,816,438 issued Mar. 28, 1989, the disclosure of which is incorporated herein by reference. Solid-phase synthesis is conducted in a manner to stepwise add amino acids in the chain beginning at the C-terminus in the manner set forth in that U.S. patent. Side-chain protecting groups, which are well known in the art, are preferably included as a part of any amino acid which has a particularly reactive side chain, and optionally may be used in the case of others such as Trp, when such amino acids are coupled onto the chain being built upon the resin. Such synthesis provides the fully protected intermediate peptidoresin.

Chemical intermediates which are used to synthesize certain preferred SRIF analogs may be represented by the formula:

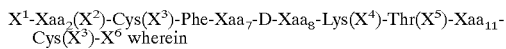

$X^1$ is an α-amino protecting group of the type known to be useful in the art in the stepwise synthesis of a polypeptide, e.g. tertbutyloxycarbonyl(Boc).

$X^2$ is hydrogen or a protecting group for the phenolic hydroxyl group of Tyr, such as 2-bromobenzyloxycarbonyl (2BrZ).

$X^3$ is hydrogen or a protecting group for Cys, such as p-methoxybenzyl(Mob) or acetamidomethyl (Acm).

$X^4$ is a protecting group for an amino side chain group, such as 2-chlorobenzyloxycarbonyl(2Cl-Z), which is not removed during deprotection of the α-amino groups during the synthesis.

$X^5$ is hydrogen or a protecting group for the hydroxyl side chain of Thr or Ser, e.g. benzyl ether(Bzl).

$X^6$ is selected from the class consisting of OH, $OCH_3$ and esters, including a benzyl ester or a hydroxymethyl ester anchoring bond used in solid-phase synthesis for linking to a solid resin support, such as —O—$CH_2$-polystyrene resin support.

Thus, there is broadly provided a method for making a SRIF analog peptide having the formula:

(cyclo 3-14)H-Xaa$_2$-Cys-Phe-Xaa$_7$-D-Xaa$_8$-Lys-Thr-Xaa$_{11}$-Cys-OH wherein Xaa$_2$, Xaa$_7$ and D-Xaa$_8$ are as set forth hereinbefore, by first forming an intermediate peptide having the formula:

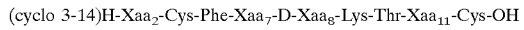

and then splitting off any protecting groups $X^1$ to $X^5$ and/or cleaving from any resin support included in $X^6$ before oxidizing to create a disulfide bond between the Cys side chains.

The SRIF analogs of the invention are generally effective at levels of less than 100 micrograms per kilogram of body weight. For prolonged action, it may be desirable to use dosage levels of about 0.1 to about 2.5 milligrams per kilogram of body weight. These analogs are soluble in water and thus can be prepared as relatively concentrated solutions for administration.

The following Examples illustrate the syntheses of a number of SRIF analog peptides embodying various features of the invention, together with the syntheses of protected amino acids for use in such peptide syntheses. All of these peptides include at least one D-isomer amino acid residue, and although the preferred SRIF analogs do not include all 14 amino acid residues of the native SRIF, to permit ready comparison with the native SRIF sequence, the peptide analogs are described by making reference to the comparable positions in the native SRIF sequence having positions 1 through 14, as is commonly done when naming analogs of a native compound. In each peptide, the cysteine residues in positions 3 and 14 are joined by the cyclizing disulfide bond.

EXAMPLE 1

Syntheses of Monomers $N^\beta$Boc-Agl(Me,Np) Synthesis

The synthesis of unresolved $N^\alpha$Boc-$N^\beta$Me(2-naphthoyl) aminoglycine, which is referred to by the shorthand nomenclature as Boc-$N^\beta$MeAgl(2-naphthoyl) or Boc-Agl(Me, 2Np), is carried out either prior to the peptide synthesis or while the peptide intermediate is on the resin. Unresolved $N^\alpha$Boc-Agl(Me,Fmoc) is first synthesized using the procedure set forth in Jiang, et al., Orthogonally protected N-methyl-substituted α-aminoglycine, *Protein and Peptide Lett.*, 3:219–224 (1996). The Fmoc protection can be removed from the monomer (or when a part of the peptide resin) with 20% piperidine in NMP, and the naphthoyl is then introduced by reaction of the free side chain secondary amino group with naphthoyl acid chloride.

Boc-L-Agl(Fmoc)-OH Synthesis

Boc-D/L-Agl(Fmoc)-OH, prepared by the synthesis set forth in Qasmi, et al., *Tetrahed, Lett.*, 34:3861–3862 (1993), (21 g, 50 mmol) is mixed with powdered, water-free $K_2CO_3$ (10 g, 100 mmol) in DMF (150 ml) and stirred in a tightly closed flask at room temperature for 10 min.; from time to time, the $CO_2$ being formed was allowed to escape. Then the mixture was cooled to 4° C. (ice bath) and $CH_3I$ (9.35 mL, 150 mmol) was added to it and closed tightly. The stirring was continued in an ice bath for 2 hours, then at room temperature for 2 hours. The reaction was monitored by HPLC on a Vydac column (0.46×25 cm, 5 mm particle size, 300 Å pore size) with a gradient running from 50% to 90% solvent B over 20 min. Solvents A and B were 0.1% TFA, and 0.1% TFA in (60% MeCN/40% $H_2O$), at a flow rate of 1.0 mL/min., with UV detection at 214 nm. When the reaction was complete, the solid was filtered and washed with DMF. The filtrate was evaporated to dryness in vacuum. The residue was crystallized from ether/petroleum ether to afford quantitative yield of tert-Butyloxycarbonyl-D/L-amino-glycine-Fluorenylmethyloxycarbonyl-glycine-methylester [Boc-D/L-Agl-(Fmoc)-OMe].

A mixture of 0.01 mol ethylenediaminetetraacetic acid (EDTA) in water (1000 mL; pH adjusted to 6.2 with 1M NaOH), 0.05 mol Cystein.HCl in water (1000 mL, pH adjusted to 6.2 with 1M NaOH), $H_2O$ (240 mL, MiliQ pure), and 0.06 mol mercaptoethanol (10 mL) was used to dissolve and activate 1 g of Papain enzyme (purchased from Acros, Fisher Scientific, Pittsburgh, Pa.) at 25° for 2 hours.

To a stirred buffer solution, which consisted of 0.1 M $Na_2HPO_4.7H_2O$ with 1.5 mM EDTA $Na_2$ in water (240 mL) and 0.1 M citric acid with 1.5 mM EDTA $Na_2$ in water (60 mL) resulting in pH 6.2, Boc-D/L-Agl(Fmoc)-OMe (21.5 g, 50 mmol) in DMF (40 mL, high purity) and MeCN (40 mL, HPLC grade) was added. Vigorous stirring of the resulting oil afforded to turn the oil into solid. Then the suspension of Papain (100 mg) and dithiothreitol (200 mg) in the same aqueous buffer (pH=6.2) was added to the reaction mixture and stirred at room temperature for 3–4 days. From time to time, fresh enzyme and activator were introduced to the mixture when the hydrolysis slowed down, rather than applying a higher concentration at the beginning. The hydrolysis was monitored by HPLC on a Vydac column (0.46×25 cm, 5 mm particle size, 300 Å pore size) with a gradient running from 50% to 90% solvent B over 20 min. Solvents A and B were 0.1% TFA and 0.1% TFA in 60% MeCN/40% $H_2O$ at a flow rate of 1.0 mL/min, with UV detection at 214 nm. The pH was maintained at 6.2 with 0.2 M $Na_2HPO_4$ solution. The L-isomer of Agl with Fmoc protection on the side chain amino hydrolyzes. The crystals of the D-isomer methylester, which separated on the wall of the flask from time to time during the process were washed in with MeCN. After the conversion could not be improved with either additional enzyme or reaction time, the pH was adjusted between 6.2–6.8 and the mixture was diluted with water to 900 mL. About 9 grams of solid Boc-Agl-(Fmoc)-OMe was removed by filtration and washed with buffer (pH=6.2) and water. It was substantially the D-isomer, but contained a small amount of the L-isomer because the enzymatic hydrolysis was not 100% complete. MS FAB:m/e 427.00 (M+H), calc.: 427.19 (M+H). It should be useful in an azide coupling scheme.

The filtrate was washed with diethyl ether (2×50 mL; the first 50 mL was dissolved in the aqueous mixture). The separated clear aqueous solution was cooled and acidified to pH 3 with solid NaHSO$_4$. Standing at 0° C. for 2–3 hours afforded 10 g (40%) of Boc-L-Agl(Fmoc)-OH, which was collected by filtration. mp:191–193 (dec.). MS FAB:m/e 412.99 (M+H), calc.:413.17 (M+H)[α]$_{D25}$=+9.8°(c=2, DMF). The purity of Boc-L-Agl(Fmoc)-OH in the analyzed sample was found to be 95% ee (enantiomeric excess); it is alternatively referred to as Boc-L-Agl(Fmoc). It is structurally the same as Fmoc-D-Agl(Boc)-OH and may be so referred to.

EXAMPLE 2

The somatostatin agonist des-AA$^{1,2,4,5,12,13}$[Tyr$^7$, N$^\beta$MeD-Agl$^8$(2-naphthoyl)]-SRIF having the structure: (cyclo)H-Cys-Phe-Tyr-D-Agl(Me,2Np)-Lys-Thr-Phe-Cys-OH is synthesized by the following solid phase methodology in a stepwise manner on a chloromethylated resin. The resin is composed of fine beads of a synthetic resin prepared by copolymerization of styrene with one to two percent divinylbenzene, with the benzene rings having been chloromethylated to create a reactive benzyl chloride type of precursor linker.

The tert-butyloxycarbonyl-S-paramethoxybenzyl derivative of Cys, i.e. Boc-Cys(Mob), is linked to the resin by a known method, such as: (1) cesium salt of the Boc-protected amino acid is kept at 50° C. in dimethylformamide (DMF) overnight or (2) Boc-protected amino acid and KF (in a molar excess) are kept at 80° C. in N-methypyrrolidone (NMP) for 24 hours. One milliequivalent of the protected Cys per milliequivalent of Cl on the resin is used. Deprotection, neutralization and addition of each amino acid is performed in accordance with a suitable schedule such as that disclosed in detail in U.S. Pat. No. 5,750,499 (May. 12, 1998). For example, couplings were mediated for 1 hour by diisopropylcarbodiimide (DIC) or DIC with N-hydroxybenzotriazole (HOBt) in dichloromethane and N-methyl-pyrrolidinone (NMP), respectively and monitored by the qualitative ninhydrin test.

A 3.0-equivalent excess of the protected amino acids based on the original substitution of the resin was used. The Boc derivatives of the next three amino acids are used; however, Fmoc-D-Agl(Boc) is then added. After α-amino deprotection of the first residue, i.e., Boc-Cys(Mob), the N$^\alpha$Boc derivatives of the next three amino acids are sequentially coupled, followed by coupling of Fmoc-D-Agl(Boc), to produce the pentapeptide Fmoc-D-Agl(Boc)-Lys(2Cl-Z)-Thr(Bzl)-Phe-Cys(Mob)-O-CH$_2$ which is linked to the resin at its C-terminus. The methylation of the side chain amino group on the Agl residue is carried out while the pentapeptide is on the resin using the technique set forth in Kaljuste, et al., *Int. J. Peptide Protein Res.*, 42:118–124, 1993. The Boc group on the side chain amino is first removed by treatment with trifluoroacetic acid (TFA, 60% in CH$_2$Cl$_2$, 2% m-cresol) for 20 min. An isopropyl alcohol (1% m-cresol) wash follows the TFA treatment, and then successive washes are carried out with triethylamine solution (10% in CH$_2$Cl$_2$), methanol, triethylamine solution, methanol and CH$_2$Cl$_2$. The resulting free amino group is then reacted with Dod-Cl (4,4'dimethoxydityl chloride), followed by reductive methylation of the Dod-alkylated amino group, treating the resin with formaldehyde and sodium cyanoborohydride in NMP. Acylation of the methyl amino side chain is then carried out by removing the Dod group from the secondary amino group with TFA (60%) and adding the naphthoyl group through reaction with its acid chloride. Removal of Na-Fmoc protecting group with 20% piperidine in NMP, in two successive 5 and 15 min. treatments, thereafter allows the elongation of the peptide backbone until completion of the octapeptide intermediate: Boc-Cys(Mob)-Phe-Tyr(2BrZ)-D-Agl(Me,2Np)-Lys(2Cl-Z)-Thr(Bzl)-Phe-Cys(Mob)-0-CH$_2$-resin support.

Cleavage of the peptide from the resin and deprotection of the side chain protecting groups are performed in hydrofluoric acid(HF) (25 ml) in the presence of 10% of anisole and 10% of dimethylsulfide for 1.5 hours at 0° C. after 20 minutes at ambient temperature. After elimination of hydrofluoric acid under high vacuum, the resin-peptide is washed with anhydrous diethyl ether.

The resin is immediately extracted with 75% acetic acid (200 ml). The extract is filtered into a 500 milliliter round-bottom flask and is then oxidized to create the disulfide cyclic linkage by stirring vigorously while rapidly adding a 10 weight percent solution of iodine in methanol until the resultant solution remains orange-colored. It is then stirred for 10–20 additional minutes and quenched with 10% ascorbic acid in water until the yellow color is gone. Concentration under vacuum is carried out to remove the acetic acid, followed by dissolution in about 250 milliliters of 60% CH$_3$CN in water. The resultant solution is diluted to about 500 milliliters with distilled water, frozen and lyophilized.

The lyophilized material is then purified by subjection to preparative RP-HPLC on a C$_{18}$ column using a linear gradient of increase of 1% B per 3 min., from the baseline %B. (Eluent A=0.25 N TEAP, pH 2.25; eluent B–60% CH$_3$CN, 40% A). Purification, in TEAP pH 2.25, is followed by a rechromatography in a 0.1% TFA solution and acetonitrile on the same cartridge (gradient of 1% acetonitrile/min). The desired cyclic peptide (cyclo)H-Cys-Phe-Tyr-D-Agl(Me,2Np)-Lys-Thr-Phe-Cys-OH is obtained which appears to be greater than 95% pure on capillary zone electrophoresis.

MS analysis shows the expected mass of 1148.2 Da. The peptide is hereinafter referred to as Peptide No. 2.

The identical peptide is also synthesized by a different route using unresolved Boc-D/L-Agl(Me,Fmoc) and carrying out the reaction on the resin with naphthoyl acid chloride after deprotection using 20% piperidine in NMP. Alternatively, Boc-D/L-Agl(Me,Np)-OH could be reacted. The reaction results in two stereoisomers of the peptide of interest. They are separable by reverse phase HPLC, and the earlier eluting isomer of the two co-elutes with the peptide referred to above as Peptide No. 2. MS also showed the same expected mass as for Peptide No. 2. When subsequently tested for binding affinity, as described hereinafter, both were shown to have binding affinities that were not statistically different.

EXAMPLE 2A

The synthesis described in Example 2 is repeated with one change. N$^\alpha$Boc-D-Cys(Mob) is used to provide the 3-position residue. Following removal of the Boc group at the N-terminus, cleavage, deprotection, cyclization and purification are carried out as in Example 2. The purified cyclic peptide has the formula:

and is referred to as Peptide No. 2A. MS analysis shows a mass of 1149.5 Da.

The second synthesis using unresolved Boc-D/L-Agl(Me, Fmoc) is also repeated using N$^\alpha$Boc-D-Cys(Mob) at the N-terminus. Following the RP-HPLC separation, two stereoisomers are obtained. The earlier eluting isomer is found to co-elute with Peptide No. 2A. MS showed a similar mass, and subsequent tests showed binding affinities that were not statistically different.

EXAMPLE 2B

The second synthesis described in Example 2 is repeated with one change. N$^\alpha$Boc-Phe is used instead of Boc-Tyr (2BrZ) to provide the 7-position residue. Further elongation of the chain then proceeds as in Example 2, and cleavage, deprotection, cyclization, and separation of stereoisomers and purification are carried out as in Example 2. The purified, cyclic peptide separated isomer has the formula:

(cyclo 3-14)H-Cys-Phe-Phe-D-Agl(Me,2Np)-Lys-Thr-Phe-Cys-OH and is referred to as Peptide No. 2B. MS analysis shows a mass of 1133.6 Da, which is expected.

EXAMPLE 2C

The second synthesis described in Example 2 is repeated with one change. N$^\alpha$Boc-4Cl-phenylalanine, i.e. Boc-4ClPhe, is used to provide the 7-position residue. Further elongation of the chain then proceeds as in Example 2, and cleavage, deprotection, cyclization, and purification and separation of stereoisomers are carried out as in Example 2. The purified, cyclic peptide separated isomer has the formula:

and is referred to as Peptide No. 2C. MS analysis shows a mass of 1286.6 Da, which is expected.

EXAMPLE 2D

The synthesis described in Example 2B is repeated with one change. N$^\alpha$Boc-D-Cys(Mob) is used to provide the 3-position residue. Following removal of the Boc group at the N-terminus, cleavage, deprotection, cyclization, and purification and separation of stereoisomers are carried out as in Example 2. The purified, cyclic peptide separated isomer has the formula:

(cyclo 3-14)H-D-Cys-Phe-Phe-D-Agl(Me,2Np)-Lys-Thr-Phe-Cys-OH and is referred to as Peptide No. 2D. MS analysis shows a mass of 1133.5 Da, which is expected.

EXAMPLE 2E

The synthesis described in Example 2C is repeated with one change. N$^\alpha$Boc-D-Cys(Mob) is used to provide the 3-position residue. Following removal of the Boc group at the N-terminus, cleavage, deprotection, cyclization, and purification and separation of isomers are carried out as in Example 2. The purified cyclic peptide separated isomer has the formula:

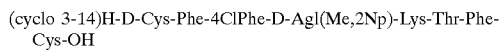

and is referred to as Peptide No. 2E. MS analysis shows a mass of 1167.4 Da, which is expected.

EXAMPLE 2F

The synthesis described in Example 2A is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction is carried out with about 1 gm of the peptidoresin and 100 mg of sodium cyanate (NaOCN) and acetic acid (3 ml) for 30 minutes at 22° C. in NMP (4 ml). This reaction results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo 3-14)Cbm-D-Cys-Phe-Tyr-D-Agl(Me,2Np)-Lys-Thr-Phe-Cys-OH and is referred to as Peptide No. 2F. MS analysis shows a mass of 1192.4 Da, which is expected.

Peptides 2, 2A, 2B, 2C, 2D, 2E and 2F bind strongly and selectively to SSTR3.

EXAMPLE 2G

The second synthesis described in Example 2A is repeated but this time residues 4, 5, 12 and 13 from SRIF are included to produce the 12-residue peptide. Cleavage, deprotection, cyclization, and purification and separation of isomers are carried out as in Example 2. The purified cyclic peptide separated isomer has the formula:

(cyclo 3-14)H-Cys-Lys-Asn-Phe-Tyr-D-Agl(Me,2Np)-Lys-Thr-Phe-Thr-Ser-Cys-OH and is referred to as Peptide No. 2G. MS analysis shows a mass of 1579.5 Da.

Peptide 2G binds selectively to SSTR3 but has fairly low affinity for all five SRIF receptors.

EXAMPLE 2H

The synthesis described in Example 2B is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction as described in Example 2F is carried out and results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo 3-14)Cbm-Cys-Phe-Phe-D-Agl(Me,2Np)-Lys-Thr-Phe-Cys-OH and is referred to as Peptide No. 2H.

EXAMPLE 2I

The synthesis described in Example 2 is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction as described in Example 2F is carried out and results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo 3-14)Cbm-Cys-Phe-Tyr-D-Agl(Me,2Np)-Lys-Thr-Phe-Cys-OH and is referred to as Peptide No. 2I.

EXAMPLE 2J

The synthesis described in Example 2D is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction as described in Example 2F is carried out and results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

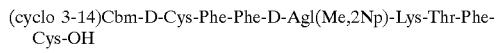
(cyclo 3-14)Cbm-D-Cys-Phe-Phe-D-Agl(Me,2Np)-Lys-Thr-Phe-Cys-OH and is referred to as Peptide No. 2J.

EXAMPLE 2K

The synthesis described in Example 2A is repeated with one change. Following removal of the Boc group at the N-terminus, a reaction is carried out with an alkyl isocyanate to add a methyl carbamoyl moiety at the N-terminus.

After deblocking the α-amino group at the N-terminus using trifluoroacetic acid (TFA), a reaction is carried out with about 1 gm of the peptidoresin and 100 mg of methyl isocyanate in the presence of 2.7 mmol of DIEA for 2 hours at 22° C. in DMF (10 ml). This reaction results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

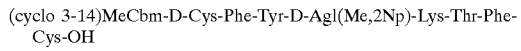
(cyclo 3-14)MeCbm-D-Cys-Phe-Tyr-D-Agl(Me,2Np)-Lys-Thr-Phe-Cys-OH and is referred to as Peptide No. 2K.

Peptides 2H–2K bind strongly and selectively to SSTR3.

EXAMPLE 2L

The synthesis described in Example 2F is repeated with one change. N$^{\alpha}$Boc-aminophenylalanine(2ClZ), i.e. Boc-Aph(2ClZ), is used to provide the 11-position residue. Further elongation of the chain then proceeds as in Example 2F, and cleavage, deprotection, cyclization, and purification and separation of stereoisomers are carried out as in Example 2F. The purified, cyclic peptide has the formula:

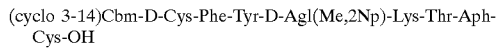
(cyclo 3-14)Cbm-D-Cys-Phe-Tyr-D-Agl(Me,2Np)-Lys-Thr-Aph-Cys-OH and is referred to as Peptide No. 2L.

EXAMPLE 2M

The synthesis described in Example 2F is again repeated, this time using Boc-Aph(Fmoc) to provide the 11-position residue. The Fmoc group is then removed by successive treatments with 25% piperidine in DMF (10 ml) for about 15 min. After washing with DMF, it is treated with acetic anhydride in DMF at room temperature for 30 minutes to acetylate the side chain amino. Following removal of the Boc group, further elongation of the chain, and reaction at the N-terminus, cleavage, deprotection, cyclization, and purification are carried out as in Example 2. The purified, cyclic peptide has the formula:

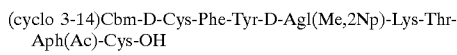
(cyclo 3-14)Cbm-D-Cys-Phe-Tyr-D-Agl(Me,2Np)-Lys-Thr-Aph(Ac)-Cys-OH and is referred to as Peptide No. 2M.

EXAMPLE 2N

The synthesis described in Example 2M is repeated with one change. The Fmoc group on the Aph residue is not removed until the entire chain is in place. Then, following removal of the Boc group at the N-terminus and the Fmoc group, a reaction is carried out to add carbamoyl moieties and thus create urea groups both at the N-terminus and on the Aph side chain.

After deblocking the α-amino group at the N-terminus using TFA and removing the Fmoc group with piperidine, reaction is carried out with about 1 gm of the peptidoresin using 100 mg of sodium cyanate (NaOCN) and acetic acid (3 ml) for 30 minutes at 22° C. in NMP (4 ml). This reaction results in the addition of the carbamoyl moiety at the N-terminus and to the Aph side chain. Thereafter, cleavage of the peptide from the resin and deprotection of the side chain protecting groups, followed by cyclization and purification, are carried out as in Example 2. The purified cyclic peptide has the formula:

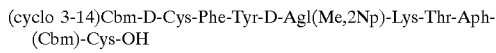
(cyclo 3-14)Cbm-D-Cys-Phe-Tyr-D-Agl(Me,2Np)-Lys-Thr-Aph-(Cbm)-Cys-OH and is referred to as Peptide No. 2N.

Peptides 2L, 2M and 2N bind strongly and selectively to SSTR3.

EXAMPLE 3

The second synthesis described in Example 2 is repeated with two changes: N$^{\alpha}$Boc-D-2Nal is used for the 8-position residue, and N$^{\alpha}$Boc-D/L-Agl(Me,Fmoc) is used to provide the 7-position residue.

After coupling Boc-D/L-Agl(Me,Fmoc) into the peptidoresin following the coupling of Boc-D-2Nal as the 8-position residue, the Fmoc-protected secondary amino group is deprotected, using 20% piperidine in NMP, and reacted with benzoyl acid chloride.

After removal of the Boc-protecting group, further elongation of the chain proceeds as in Example 2 through the final coupling with Boc-Cys(Mob) at the N-terminus, and the Boc group at the N-terminus is removed by treatment with 60% TFA in DCM for 20 minutes. Cleavage, deprotection and cyclization are then carried out as in Example 2. The cyclized peptide is then purified by subjection to analytical HPLC on a $C_{18}$ column. Peaks are located which are then individually purified using similar buffer systems. Final analytical HPLC is carried out as generally described with respect to Example 2. The desired cyclic octapeptides are obtained in the form of two separate stereoisomers. The purified cyclic peptide having the L-isomer of Agl is selected. It has the formula:

(cyclo 3-14)H-Cys-Phe-Agl(Me,Bz)-D-2Nal-Lys-Thr-Phe-Cys-OH and is referred to as Peptide No. 3. MS analysis shows a mass of 1133.4 Da.

EXAMPLE 3A

The synthesis described in Example 3 is repeated with one change. $N^\alpha$Boc-D-Cys(Mob) is used instead of $N^\alpha$Boc-Cys (Mob). Cleavage, deprotection, cyclization, and purification and separation of isomers are carried out as in Example 3. The separated, purified, cyclic peptide containing the L-isomer of Agl has the formula:

(cyclo 3-14)H-D-Cys-Phe-Agl(NMe,Bz)-D-2Nal-Lys-Thr-Phe-Cys-OH and is referred to as Peptide No. 3A.

Peptide Nos. 3 and 3A bind selectively to SSTR3.

EXAMPLE 3B

The synthesis of Example 3 is repeated again, substituting $N^\alpha$Boc-D-1Nal for $N^\alpha$Boc-D-2Nal to obtain the following separated, purified, cyclic peptide, which is referred to as Peptide No. 3B:

(cyclo 3-14)H-Cys-Phe-Agl(Me,Bz)-D-1Nal-Lys-Thr-Phe-Cys-OH.

EXAMPLE 3C

The synthesis described in Example 2A is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction as described in Example 2F is carried out and results in the addition of the carbamoyl moiety at the N-terminus. Thereafter, cleavage of the peptide from the resin and deprotection of the side chain protecting groups, followed by cyclization and purification, are carried out as in Example 1. The purified cyclic peptide has the formula:

(cyclo 3-14)Cbm-D-Cys-Phe-Agl(NMe,Bz)-D-2Nal-Lys-Thr-Phe-Cys-OH and is referred to as Peptide No. 3C.

Peptides Nos. 3B and 3C bind selectively to human SSTR3.

EXAMPLE 4

The synthesis described in Example 2B is repeated with one change. Elongation of the chain by one residue is carried out by coupling $N^\alpha$Boc-Tyr(2BrZ) at the N-terminus.

Cleavage, deprotection, cyclization, and purification and separation of isomers are carried out as in Example 2B. The purified, cyclic peptide, separated isomer has the formula:

(cyclo)H-Tyr-Cys-Phe-Phe-D-Agl(Me,2Np)-Lys-Thr-Phe-Cys-OH and is referred to as Peptide No. 4. The peptide is readily radioiodinated with $^{125}$I to provide a ligand for use in competitive drug screening assays. Following radioiodination, it continues to bind strongly to SSTR3. Instead of including Tyr at the N-terminus, Tyr can alternatively be substituted for Phe in the 11-position, adjacent Cys at the C-terminus. The resultant analog also binds strongly and may be preferred.

In vitro Bioassay: The various somatostatin analogs are tested in vitro for their ability to bind to isolated cloned receptors expressed on CHO-K1 cells and CCL39 cells. CHO-K1 cells are grown in Ham's F-12 medium, and CCL39 cells are grown in Dulbecco's modified Eagle's medium/Ham's F-12(1:1) mix, supplemented with 10% fetal bovine serum, 100 U/ml penicillin and 100 μg/ml streptomycin, in humidified air containing 5% $CO_2$ at 37° C.

The molecular cloning of the genes encoding multiple somatostatin receptor subtypes permits the individual expression of these receptors in mammalian cells and the characterization of their respective pharmacological profiles. Five such receptor subtypes, termed SSTR1 through SSTR5, have been cloned and are reported and described in Raynor et al., *Molecular Pharmacology*, 43, 838–844 (1993) and in Raynor et al., *Molecular Pharmacology*, 44, 385–392 (1993). These references describe binding assays that can be used to determine whether particular SRIF analogs bind selectively to one or more of the 5 receptor types and also whether they bind to such receptor types with high or low affinity. Because these receptor types have now generally been characterized with regard to their pharmacological profiles, knowledge of the results of such binding studies, along with knowledge of the unique patterns of distribution of these receptors in the body indicate that each receptor subtype may mediate distinct but overlapping physiological effects of SRIF. As a result, compounds which bind selectively to receptors SSTR3, for example, can be used to modulate a particular physiological function of SRIF without potentially having an undesired effect resulting from another physiological function of SRIF which is mediated by other SRIF receptors.

Cells are washed twice with and scraped into ice-cold 0.05 M Tris-HCl (pH 7.4), collected by centrifugation, and homogenized using a rotor/stator slash system in the same buffer. After centrifugation at 120 g for 5 min. at 4° C., the supernatant is collected and centrifuged again at 48,000 g for 30 min. at 4° C. The resulting pellet is resuspended in ice-cold Tris buffer, transferred into a microfuge tube, and centrifuged at 20,000 g for 15 min. at 4° C. After withdrawal of the supernatant, the membrane pellet is stored at −80° C.

Receptor autoradiography is performed on 20 μm thick cryostat sections of the membrane pellets, mounted on microscope slides, and then stored at −20° C. For each of the tested compounds, complete displacement experiments are performed with the universal somatostatin ligand radioligand $^{125}$I-[Leu$^8$,D-Trp$^{22}$,Tyr$^{25}$]-somatostatin-28 that binds with strong affinity to all five receptors. Increasing concentrations of the unlabeled peptide are used ranging from 0.1–1000 nM. Unlabeled somatostatin-28 is run in parallel using the same increasing concentrations, as a control. $IC_{50}$ values are calculated after quantification of the data using a computer-assisted image processing system as known in this art. At concentrations of 100 nM, Peptide No. 2 had minimal effects on the binding of the SRIF-28 radioligand to human SSTR1, SSTR2, SSTR4 and SSTR5. In contrast, it selectively bound to SSTR3, displacing the binding of the radioligand to human SSTR3 with an $IC_{50}$ value of about 70 nM. Peptide No. 2A containing the D-Cys$^3$ modification selectively binds to SSTR3, and exhibits a lower $IC_{50}$ of about 39 nM. Peptide No. 2B, the analog without the Tyr$^7$ modification, also selectively binds to SSTR3, exhibiting an $IC_{50}$ of about the same as No. 2. The addition of a carbamoyl or an alkyl carbamoyl to the N-terminus significantly lowers the $IC_{50}$ of these analogs, with Peptide 2F having a binding strength essentially equal to that of SRIF-28. Peptide No. 3 likewise selectively binds SSTR3; it exhibits an $IC_{50}$ of about 80 nM. Peptides 2C, 2D and 2E are slightly less selective. However, the binding affinity may be improved without significantly detracting from the selectivity by replacing Phe in the 11-position by Aph, Aph(Ac) or Aph (Cbm).

To investigate whether an iodinated analog may serve as a selective SSTR3 radioligand, Peptide No. 4, i.e. the N-terminus-extended, $Tyr^2$ analog, of Peptide No. 2B is synthesized, iodinated and tested for binding to the five cloned SRIF receptors. No specific binding of Peptide No. 4 to SSTR1, 2, 4 and 5 is detectable. In contrast, Peptide No. 4 effectively binds to SSTR3 to about the same extent as Peptide No. 2B, and its binding strength can be improved by acylation of the Tyr with carbamoyl (with its phenolic hydroxyl protected) and/or by the substitution of Aph(X). Moreover, iodination of $Tyr^{11}$ may provide improved binding compared to the comparable $Tyr^2$ analog.

Screening assays, as are well known in the art which employ the receptor polypeptide SSTR3 directly from the recombinant host, can be used to identify agents useful in blocking or mimicking certain aspects of somatostatin as desired while eliminating the undesirable aspects of the hormone which may arise from activation or blocking of other receptors.

The potencies of certain SRIF analogs to inhibit radioligand binding of $^{125}I$-[$Leu^8$,D-$Trp^{22}$,$Tyr^{24}$]SRIF-28 to the various cloned SRIF receptors are shown in the following table wherein the $IC_{50}$ values are given in nanomolar concentration.

TABLE

| Compound | $IC_{50}$ (nM) | | | | |
|---|---|---|---|---|---|
| | mSSTR1 | mSSTR2 | mSSTR3 | mSSTR4 | mSSTR5 |
| Peptide No. 2 | >10,000 | >10,000 | 70 ± 18 | >1,000 | >10,000 |
| Peptide No. 2A | >10,000 | >10,000 | 39 ± 11 | >10,000 | >10,000 |
| Peptide No. 2B | >10,000 | >10,000 | 70 ± 17 | >10,000 | >10,000 |
| Peptide No. 2C | >1,000 | >1,000 | 300 | >10,000 | >10,000 |
| Peptide No. 2D | >10,000 | >10,000 | 115 ± 36 | >10,000 | >1,000 |
| Peptide No. 2E | >1,000 | >1,000 | 180 | >10,000 | >1,000 |
| Peptide No. 2F | >10,000 | >10,000 | 6.7 ± 2.6 | >10,000 | >10,000 |
| Peptide No. 3 | >10,000 | >1,000 | 80 | >1,000 | >1,000 |

It is of interest to consider the relative potency of these SRIF analogs, based upon their binding affinity, by comparison to SRIF-28 which, as indicated hereinbefore, binds strongly to all five receptors. For example, the relative potency of Peptides Nos. 2 and 2B is about 0.13, i.e. they bind to SSTR3 with a strength equal to about 13% of that of SRIF-28. Peptide No. 2D has a relative potency of about 0.08, whereas Peptide No. 2A has a potency of about 0.24. In contrast, Peptide No. 2F has a relative potency of about 1.4 that is better than SRIF-28, i.e. it shows about 40% greater affinity. These SRIF analogs that are selective for SSTR3 and that have been tested were found to generally be functional inhibitors of SRIF, so they can accordingly be used to block the activation of the SSTR3 receptors.

The peptides of the invention not only provide more selective ligands for binding SSTR3 but the use of labeled Peptide No. 4, or Peptide No. 2 or the $Tyr^{11}$ analog labeled, e.g. with $^{125}I$, facilitates drug screening for even more effective antagonists. Competitive binding assays with candidate compounds would first be carried in this manner with SSTR3 to search for high binding affinity; then by screening the multiple SRIF receptors, it could be confirmed whether there was selective binding to only this receptor, as is desired.

Because, as shown above, additions to the N-terminus of the SRIF analog do not appear to adversely affect the selective binding, it should be clear that these compounds can be complexed with a cytotoxic or a radioactive agent for the purpose of carrying that agent to a tumor or other tissue for which degradation is desired. For example, a dialdehyde linker such as glutaraldehyde may be used to link the SRIF analog to saporin or gelonin. Likewise, linkers such as DOTA or DTPA or other suitable chelating agents can be used to complex the SRIF analog with a highly radioactive element as indicated hereinbefore. If desired, the solubility of the SRIF analogs can be improved by acylation of the N-terminal amino group using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the SRIF analog as known in this art.

These SRIF analogs or nontoxic salts thereof, combined with a pharmaceutically or veterinarily acceptable carrier to form a pharmaceutical composition, may be administered to animals, including humans and other mammals, either intravenously, subcutaneously, intramuscularly, percutaneously, e.g. intranasally, intracerebrospinally or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans should be under the direction of a physician to combat specific tumors and cancers or to mediate other conditions where the SSTR3 receptors exert a control function, such as coupling to a tyrosine phosphatase so that stimulation of this enzyme can be carried out to mediate the anti-proliferative effects of SRIF. The required dosage will vary with the particular condition being treated, with the severity of the condition and with the duration of desired treatment.

Such peptides are often administered in the form of pharmaceutically or veterinarily acceptable nontoxic salts, such as acid addition salts or metal complexes, e.g., with zinc, iron, calcium, barium, magnesium, aluminum or the like. Illustrative of such nontoxic salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver these SRIF analogs over prolonged periods of time, for example, for periods of one week to one year from a single administration, and slow release, depot or implant dosage forms may be utilized as well known in this art. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain an SRIF analog or a salt thereof dispersed or encapsulated in a slow degrading, non-toxic or non-antigenic polymer such as a polylactic acid/polyglycolic acid polymer, for example, as described in U.S. Pat. No. 3,773,919.

Therapeutically effective amounts of the peptides should be administered under the guidance of a physician, and pharmaceutical compositions will usually contain the peptide in conjunction with a conventional, pharmaceutically or veterinarily-acceptable carrier. A therapeutically effective amount is considered to be a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as earlier described. A therapeutically effective amount is typically an amount of an SRIF analog that, when administered peripherally, e.g. intravenously, in a physiologically acceptable composition, is sufficient to achieve a plasma concentration thereof from about 0.1 $\mu$g/ml to about 100 $\mu$g/ml, preferably from about 1 $\mu$g/ml to about 50 $\mu$g/ml, more preferably at least about 2 $\mu$g/ml and usually 5 to 10 $\mu$g/ml. In these amounts, they may be used to desirably affect gastric secretion.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. Although the claims variously define the invention in terms of a peptide sequence, it should be understood that such is intended to include nontoxic salts thereof which are well known to be the full equivalent thereof and which are most frequently administered. Instead of the simple free acid at the C-terminus, a lower alkyl ester or amide may be incorporated as well known in the peptide art. Cyclic peptides having an amino acid residue sequence substantially identical to the sequence of the SRIF analogs specifically shown herein, in which one or more residues have been conservatively substituted with a functionally similar amino acid residue, are considered to be equivalents so long as they selectively bind to SSTR3.

As previously indicated, these specified modifications can be incorporated in previously disclosed SRIF analogs to create SSTR3-selectivity. Although not preferred, one or two of the deleted residues in the ring portion may be included; for example, incorporation of a residue, such as Asn, in the 5-position is considered optional. Likewise, inclusion of residues in the 1- and 2-position is optional, but except for Tyr, D-Tyr, D-Ala or an acyl group, such elongation is not considered worthwhile. Often a complexing agent will be linked to the α-amino group at the N-terminus of these peptides which is capable of joining thereto a radioactive nuclide or a cytotoxin. Broadly it is considered that a preferred group of cyclic somatostatin analog peptides can be created having specific affinity for the SRIF receptor SSTR3 by modifying the amino acid sequence of existing SRIF analogs which are known in the art to exhibit SRIF biological activity. The modified peptide should have an amino acid sequence at least 8 residues in length, contain a Cys-Cys disulfide bond with a sequence of at least 6 residues located between such Cys residues as a ring structure, and contain Phe-Xaa$_7$-D-Xaa$_8$-Lys-Thr or its equivalent generally adjacent the N-terminal Cys of the ring structure; these SRIF analog peptides are characterized preferably by the presence of D-Xaa$_8$ in the form of N$^\beta$MeD-Agl(2-naphthoyl) with Xaa$_7$ being Tyr or Phe (as defined hereinbefore) or alternatively by Xaa$_7$ being N$^\beta$MeAgl(2-benzoyl) with Xaa$_8$ being D-2Nal or an equivalent, as defined hereinbefore. The disclosed cyclic SRIF analogs may also be modified by N-methylation of the α-amino group on one (or two) of the residues in this 6-residue central sequence to create resulting SRIF analogs that retain their specificity for SSTR3 and, in some instances, may have even greater binding affinity. Such peptides and salts thereof are considered as being within the scope of the claimed invention.

The inclusion of a carbamoyl moiety or a lower alkyl carbamoyl, preferably methyl, ethyl or isopropyl, at the N-terminus of any of these analogs improves binding strength without detracting from selectivity. More importantly, this effect is found to be applicable to all cyclic octapeptide analogs of somatostatin regardless of whether they are selective for SSTR3, for some other SSTR, or not truly selective at all, so long as they are cyclized by a cysteine-cysteine bond or the equivalent thereof and contain at least 6 residues in the ring itself. For example, the incorporation of Cbm at the N-terminus of ODT8 or Octreotide, as well as those analogs set forth in the foregoing Examples, significantly increases binding affinity to various of the SSTRs and is expected to also increase the duration of biological activity following administration.

The disclosures of all patents and publications set forth hereinbefore are expressly incorporated herein by reference. As used herein, all temperatures are ° C. and all ratios are by volume. Percentages of liquid materials are also by volume.

Various features of the invention are emphasized in the claims which follow.

What is claimed is:

1. A cyclic somatostatin(SRIF) analog peptide which selectively binds the SRIF receptor SSTR3 in contrast to other SRIF receptors, wherein said peptide has the amino acid sequence (cyclo 3-14)Xaa$_1$-Xaa$_2$-Xaa$_3$-Phe-Xaa$_7$-D-Xaa$_8$-Lys-Thr-Xaa$_{11}$-Cys wherein Xaa$_1$ is des-Xaa, D-Ala, Ala, Cbm, L-Hor or an acyl group having up to 20 carbon atoms; Xaa$_2$ is Tyr, D-Tyr, Gly or des-Xaa; Xaa$_3$ is Cys or D-Cys; Xaa$_7$ is an amino acid selected from the group consisting of (A)Phe, Tyr or N$^\beta$MeAgl(Bz) wherein A is H, Cl, F, Br, NO$_3$, Me, OMe or NH(Q) where Q is H, Cbm or L-Hor; D-Xaa$_8$ is an amino acid selected from the group consisting of D-Nal and N$^\beta$MeD-Agl(Np); and Xaa$_{11}$ is Phe, Aph(X) or Tyr with X being H, Ac or Cbm; provided that either Xaa$_7$ is N$^\beta$MeAgl(Bz) or D-Xaa$_8$ is N$^\beta$MeD-Agl(Np).

2. The peptide according to claim 1 wherein Xaa$_1$ and Xaa$_2$ are des-Xaa.

3. The peptide according to claim 1 wherein D-Xaa$_8$ is N$^\beta$MeD-Agl(Np) and Xaa$_7$ is (A)Phe or Tyr.

4. The peptide according to claim 3 wherein Xaa$_3$ is D-Cys.

5. The peptide according to claim 3 wherein D-Xaa$_8$ is N$^\beta$MeD-Agl(2-naphthoyl).

6. The peptide according to claim 5 wherein $Xaa_7$ is Tyr.

7. The peptide according to claim 6 wherein $Xaa_3$ is D-Cys.

8. The peptide according to claim 1 wherein $Xaa_7$ is $N^\beta MeAgl(Bz)$ and $D-Xaa_8$ is D-2Nal.

9. The peptide according to claim 1 wherein there is present at the N-terminus a complexing agent capable of joining thereto a radioactive nuclide or a conjugating agent for linking to a cytotoxin.

10. The peptide according to claim 1 having the amino acid sequence: (cyclo 3-14)$Xaa_1$-$Xaa_2$-$Xaa_3$-Phe-$Xaa_7$-D-$Xaa_8$-Lys-Thr-$Xaa_{11}$-Cys wherein $Xaa_1$ is Cbm; $Xaa_2$ is Tyr, D-Tyr or des-Xaa; $Xaa_3$ is Cys or D-Cys; $Xaa_7$ is (A)Phe or Tyr; and $D-Xaa_8$ is $N^\beta MeD-Agl(Np)$.

11. The peptide according to claim 1 having the amino acid sequence: (cyclo 3-14)$Xaa_1$-D-Cys-Phe-$Xaa_7$-$N^\beta MeD$-Agl(2-naphthoyl)-Lys-Thr-$Xaa_{11}$-Cys, wherein $Xaa_1$ is Cbm or des-Xaa; $Xaa_7$ is Phe or Tyr and $Xaa_{11}$ is Phe or Aph(X).

12. A pharmaceutical composition comprising a mixture of the peptide according to claim 1 and at least one pharmaceutically acceptable carrier.

13. A cyclic somatostatin (SRIF) analog peptide having specific affinity for the SRIF receptor SSTR3 greater than its affinity for other SRIF receptors, wherein said peptide has an amino acid sequence at least 8 residues in length, contains a Cys-Cys disulfide bond with a sequence of at least 6 residues located between said Cys residues as a ring, and contains Phe-$Xaa_7$-D-$Xaa_8$-Lys-Thr adjacent to the Cys residue near the N-terminus, wherein said analog comprises either $N^\beta MeD-Agl(2-naphthoyl)$ at position $D-Xaa_8$ and Phe or Tyr at position $Xaa_7$ or $N^\beta Me-Agl(2-benzoyl)$ at position $Xaa_7$ and D-2Nal at position $D-Xaa_8$.

14. The peptide according to claim 13 wherein $D-Xaa_8$ is $N^\beta MeD-Agl(2-naphthoyl)$ and Cbm is present at the N-terminus.

* * * * *